(12) United States Patent
Kozian et al.

(10) Patent No.: US 8,071,297 B2
(45) Date of Patent: Dec. 6, 2011

(54) METHOD FOR THE DIAGNOSIS AND TREATMENT OF CARDIOVASCULAR DISEASES

(75) Inventors: Detlef Kozian, Frankfurt am Main (DE); Matthias Herrmann, Frankfurt am Main (DE); Thomas Leeuw, Frankfurt am Main (DE); Wilfried Renner, Graz (AT); Winfried Maerz, Offenbach (DE)

(73) Assignee: Sanofi-Aventis, Paris (FR)

( * ) Notice: Subject to any disclaimer, the term of this patent is extended or adjusted under 35 U.S.C. 154(b) by 81 days.

(21) Appl. No.: 12/095,783

(22) PCT Filed: Nov. 23, 2006

(86) PCT No.: PCT/EP2006/011220
§ 371 (c)(1),
(2), (4) Date: Jan. 27, 2009

(87) PCT Pub. No.: WO2007/065562
PCT Pub. Date: Jun. 14, 2007

(65) Prior Publication Data
US 2009/0239218 A1    Sep. 24, 2009

(30) Foreign Application Priority Data
Dec. 6, 2005  (EP) .................... 05026569

(51) Int. Cl.
*C12Q 1/68* (2006.01)
*C12P 19/34* (2006.01)
*C07H 21/02* (2006.01)

(52) U.S. Cl. ....... 435/6.1; 435/91.2; 536/23.1; 536/24.3

(58) Field of Classification Search .......... None
See application file for complete search history.

(56) References Cited

U.S. PATENT DOCUMENTS
5,744,305 A    4/1998   Fodor et al.
2003/0211525 A1   11/2003   Walker et al.

FOREIGN PATENT DOCUMENTS
| EP | 0916336 A1 | 5/1999 |
|---|---|---|
| WO | WO 97/11689 | 4/1997 |
| WO | WO 97/35584 | 10/1997 |
| WO | WO 98/23291 | 6/1998 |
| WO | WO 01/88188 | 11/2001 |

OTHER PUBLICATIONS

GenBank locus BC000442 (Nov. 6, 2003) '*Homo sapiens* aurora kinase B, mRNA (cDNA clone Image:2820719), partial cds.' GI: 38197154, from www.ncbi.nlm.nih.gov, pp. 1-4.*
iHOP—Information Hyperlinked over Proteins for gene symbol ARK2, from www.ihop-net.org, printed on Sep. 15, 2010, 1 page.*
Pennsis E. Science (Sep. 18, 1998) vol. 281, pp. 1787-1789.*
Hacker U.T. et al. Gut (May 1997) vol. 40, No. 5, pp. 623-627.*
Juppner H. Bone (Aug. 1995) vol. 17, No. 2, Supplement, pp. 39S-42S.*
SNP-GeneID9212, http://www.ncbi.nlm.nih.gov/SNP/snp_ref.cgi?locusid=9212, May 25, 2006.
Braun et al., Diffential Gene Evression During Intestinal Ischemia-Reperfusion Injury, Transplanation Proceedings, vol. 34. 2002, pp. 2301-2302.
DeScamps, Two Mammalian Mitotic Aurora Kinases Who's Who?, Science, STKE, vol. 173, 2001, pp. 1-4.
Kozian, Comparative gene-expression analysis, Trends in Biotechnology, vol. 17, No. 2, 1999, pp. 73-78.
Ota et al., Increases Mitotic Phosphorylation of Histone H3 Attributabel to AIM-1/Aurora-B Overexpression Contributes to Chromosome Number Instability, Cancer Research, vol. 62, Sep. 15, 2002, pp. 5168-5177.
Schobel, New Donor-Acceptor Pair for Fluorescent Immunoassays by Energy Transfer, Bioconjugate Chem, 1999, vol. 10, pp. 1107-1114.
Shi, M., Technologies for Individual Genotyping, Am. J. Pharmacogenomics, vol. 2, No. 3, 2002, pp. 197-205.
Shindo et al., cDNA Cloning, Expression, Subcellular Localization, and Chromosomal Assignment of Mammalian Aurora Homologues, Aurora-Related Kinase (ARK)1 and 2. Biochem & Biophys Res Comm., vol. 244, 1998, pp. 285-292.
Vankayalapati el al,, Targeting Aurora2 Kinase in Oncogenesis: A Structural Bioinformatics Approach to Target Validation and Rational Drug Design, Molecular Cancer Therapeutics, vol. 2, Mar. 2003, pp. 283-294.
Database DSNP (Online) ncbi; C050T SNP ARK2, Aug. 29, 2001, refSNP ID: RS2241909 XP002372732, retrieved from NCBI Database accession No. RS2241909, the whole document.
Database DBSNP (Online) ncbi; C950T SNP ARK2, Oct. 16, 2000. "refSNP ID: RS1059476" XP002372733, retrieved from NCBI Database accession No. RS2241909, the whole document.
Gene-AURKB, http://www.ensembl.org/Homo_sapiens/genesnpview?db=&gene=ENSG00000178999, Mar. 2010.

* cited by examiner

*Primary Examiner* — Stephen Kapushoc
(74) *Attorney, Agent, or Firm* — J. Darrell Pontenot

(57) ABSTRACT

The present invention refers to a method for the in vitro or in vivo diagnosis of cardiovascular diseases, in particular high blood pressure, stenosis, vessel occlusion and/or other thrombotic events, wherein the nucleotide at position 950 of a nucleic acid coding for the human ARK2 protein or the amino acid at position 298 of the human ARK2 protein of a sample of a person is determined as well as to the use of ARK2 for the development and/or production of a medicament for treating a cardiovascular disease.

7 Claims, 4 Drawing Sheets

Figure 1A

```
   1 ggccgggaga gtagcagtgc cttggacccc agctctcctc cccctttctc tctaaggatg
  61 gcccagaagg agaactccta cccctggccc tacggccgac agacggctcc atctggcctg
 121 agcaccctgc cccagcgagt cctccggaaa gagcctgtca ccccatctgc acttgtcctc
 181 atgagccgct ccaatgtcca gcccacagct gcccctggcc agaaggtgat ggagaatagc
 241 agtgggacac ccgacatctt aacgcggcac ttcacaattg atgactttga gattgggcgt
 301 cctctgggca aaggcaagtt tggaaacgtg tacttggctc gggagaagaa aagccatttc
 361 atcgtggcgc tcaaggtcct cttcaagtcc cagatagaga aggagggcgt ggagcatcag
 421 ctgcgcagag agatcgaaat ccaggcccac ctgcaccatc caacatcct gcgtctctac
 481 aactattttt atgaccggag gaggatctac ttgattctag agtatgcccc ccgcggggag
 541 ctctacaagg agctgcagaa gagctgcaca tttgacgagc agcaacagc cacgatcatg
 601 gaggagttgg cagatgctct aatgtactgc catgggaaga aggtgattca cagagacata
 661 aagccagaaa atctgctctt agggctcaag ggagagctga agattgctga cttcggctgg
 721 tctgtgcatg cgccctccct gaggaggaag acaatgtgtg gcaccctgga ctacctgccc
 781 ccagagatga ttgaggggcg catgcacaat gagaaggtgg atctgtggtg cattggagtg
 841 ctttgctatg agctgctggt ggggaaccca cccttgaga gtgcatcaca caacgagacc
 901 tatcgccgca tcgtcaaggt ggacctaaag ttccccgctt ctgtgcccac gggagcccag
 961 gacctcatct ccaaactgct caggcataac ccctcggaac ggctgccct ggcccaggtc
1021 tcagcccacc cttgggtccg ggccaactct cggagggtgc tgcctccctc tgcccttcaa
1081 tctgtcgcct gatggtccct gtcattcact cgggtgcgtg tgtttgtatg tctgtgtatg
1141 tataggggaa agaagggatc cctaactgtt cccttatctg ttttctacct cctcctttgt
1201 ttaataaagg ctgaagcttt ttgt
```

Figure 1B

```
179461 TCCAAACAGA ATGGGTAGTC AAGGAAGATG TAGCCAGGGT GAAACTAATG CAGCCCTTCC
179521 ATCTCTTCAC ACCTGCAGGT GGACCTAAAG TTCCCCGCTT CCGTGCCCAT GGGAGCCCAG
179581 GACCTCATCT CCAAACTGCT CAGGCATAAC CCCTCGGAAC GGCTGCCCCT GGCCCAGGTC
179641 TCAGCCCACC CTTGGGTCCG GGCCAACTCT CGGAGGGTGC TGCCTCCCTC TGCCCTTCAA
```

Figure 2

MAQKENSYPWPYGRQTAPSGLSTLPQRVLRKEPVTPSALVLMSRSNVQPTAAPGQKVMENSSG
TPDILTRHFTIDDFEIGRPLGKGKFGNVYLAREKKSHFIVALKVLFKSQIEKEGVEHQLRREI
EIQAHLHHPNILRLYNYFYDRRRIYLILEYAPRGELYKELQKSCTFDEQRTATIMEELADALM
YCHGKKVIHRDIKPENLLLGLKGELKIADFGWSVHAPSLRRKTMCGTLDYLPPEMIEGRMHNE
KVDLWCIGVLCYELLVGNPPFESASHNETYRRIVKVDLKFPASVPTGAQDLISKLLRHNPSER
LPLAQVSAHPWVRANSRRVLPPSALQSVA

Figure 3

```
   1 ggccgggaga gtagcagtgc cttggacccc agctctcctc cccctttctc tctaaggatg
  61 gcccagaagg agaactccta cccctggccc tacggccgac agacggctcc atctggcctg
 121 agcaccctgc cccagcgagt cctccggaaa gagcctgtca ccccatctgc acttgtcctc
 181 atgagccgct ccaatgtcca gcccacagct gcccctggcc agaaggtgat ggagaatagc
 241 agtgggacac ccgacatctt aacgcggcac ttcacaattg atgactttga gattgggcgt
 301 cctctgggca aaggcaagtt tggaaacgtg tacttggctc gggagaagaa aagccatttc
 361 atcgtggcgc tcaaggtcct cttcaagtcc cagatagaga aggagggcgt ggagcatcag
 421 ctgcgcagag agatcgaaat ccaggcccac ctgcaccatc ccaacatcct gcgtctctac
 481 aactatttt atgaccggag gaggatctac ttgattctag agtatgcccc ccgcggggag
 541 ctctacaagg agctgcagaa gagctgcaca tttgacgagc agcgaacagc cacgatcatg
 601 gaggagttgg cagatgctct aatgtactgc catgggaaga aggtgattca cagagacata
 661 aagccagaaa atctgctctt agggctcaag ggagagctga agattgctga cttcggctgg
 721 tctgtgcatg cgccctccct gaggaggaag acaatgtgtg gcaccctgga ctacctgccc
 781 ccagagatga ttgaggggcg catgcacaat gagaaggtgg atctgtggtg cattggagtg
 841 ctttgctatg agctgctggt ggggaaccca cccttgaga gtgcatcaca caacgagacc
 901 tatcgccgca tcgtcaaggt ggacctaaag ttccccgctt ctgtgcccat gggagcccag
 961 gacctcatct ccaaactgct caggcataac ccctcggaac ggctgcccct ggcccaggtc
1021 tcagcccacc cttgggtccg ggccaactct cggagggtgc tgcctccctc tgcccttcaa
1081 tctgtcgcct gatggtccct gtcattcact cgggtgcgtg tgtttgtatg tctgtgtatg
1141 tataggggaa agaagggatc cctaactgtt cccttatctg ttttctacct cctcctttgt
1201 ttaataaagg ctgaagcttt tgt
```

Figure 4

MAQKENSYPWPYGRQTAPSGLSTLPQRVLRKEPVTPSALVLMSRSNVQPTAAPGQKVMENSSG
TPDILTRHFTIDDFEIGRPLGKGKFGNVYLAREKKSHFIVALKVLFKSQIEKEGVEHQLRREI
EIQAHLHHPNILRLYNYFYDRRRIYLILEYAPRGELYKELQKSCTFDEQRTATIMEELADALM
YCHGKKVIHRDIKPENLLLGLKGELKIADFGWSVHAPSLRRKTMCGTLDYLPPEMIEGRMHNE
KVDLWCIGVLCYELLVGNPPFESASHNETYRRIVKVDLKFPASVPM̲GAQDLISKLLRHNPSER
LPLAQVSAHPWVRANSRRVLPPSALQSVA

SEQUENCE LISTING

<160> NUMBER OF SEQ ID NOS: 9

<210> SEQ ID NO 1
<211> LENGTH: 1224
<212> TYPE: DNA
<213> ORGANISM: Homo sapiens

<400> SEQUENCE: 1
ggccgggaga gtagcagtgc cttggacccc agctctcctc cccctttctc tctaaggatg     60

-continued

```
gcccagaagg agaactccta cccctggccc tacggccgac agacggctcc atctggcctg    120
agcaccctgc cccagcgagt cctccggaaa gagcctgtca ccccatctgc acttgtcctc    180
atgagccgct ccaatgtcca gcccacagct gcccctggcc agaaggtgat ggagaatagc    240
agtgggacac ccgacatctt aacgcggcac ttcacaattg atgactttga gattgggcgt    300
cctctgggca aaggcaagtt tggaaacgtg tacttggctc gggagaagaa aagccatttc    360
atcgtggcgc tcaaggtcct cttcaagtcc cagatagaga aggagggcgt ggagcatcag    420
ctgcgcagag agatcgaaat ccaggcccac ctgcaccatc ccaacatcct gcgtctctac    480 aactatttt atgaccggag gaggatctac ttgattctag agtatgcccc cgcggggag    540 ctctacaagg agctgcagaa gagctgcaca tttgacgagc agcgaacagc cacgatcatg    600
gaggagttgg cagatgctct aatgtactgc catgggaaga aggtgattca gagagacata    660
aagccagaaa atctgctctt agggctcaag ggagagctga agattgctga cttcggctgg    720
tctgtgcatg cgccctccct gaggaggaag acaatgtgtg gcaccctgga ctacctgccc    780
ccagagatga ttgagggggcg catgcacaat gagaaggtgg atctgtggtg cattggagtg    840
ctttgctatg agctgctggt ggggaaccca ccctttgaga gtgcatcaca caacgagacc    900
tatcgccgca tcgtcaaggt ggacctaaag ttccccgctt ctgtgcccac gggagcccag    960
gacctcatct ccaaactgct caggcataac ccctcggaac ggctgcccct ggcccaggtc   1020
tcagcccacc cttgggtccg ggccaactct cggagggtgc tgcctccctc tgcccttcaa   1080
tctgtcgcct gatggtccct gtcattcact cgggtgcgtg tgtttgtatg tctgtgtatg   1140 tatagggggaa agaagggatc cctaactgtt cccttatctg ttttctacct cctcctttgt   1200
ttaataaagg ctgaagcttt ttgt                                         1224
```

<210> SEQ ID NO 2
<211> LENGTH: 240
<212> TYPE: DNA
<213> ORGANISM: Homo sapiens

<400> SEQUENCE: 2

```
tccaaacaga atgggtagtc aaggaagatg tagccagggt gaaactaatg cagcccttcc     60
atctcttcac acctgcaggt ggacctaaag ttccccgctt ccgtgcccat gggagcccag    120
gacctcatct ccaaactgct caggcataac ccctcggaac ggctgcccct ggcccaggtc    180
tcagcccacc cttgggtccg ggccaactct cggagggtgc tgcctccctc tgcccttcaa    240
```

<210> SEQ ID NO 3
<211> LENGTH: 344
<212> TYPE: PRT
<213> ORGANISM: Homo sapiens

<400> SEQUENCE: 3

```
Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80
```

```
Arg Pro Leu Gly Lys Gly Lys Phe Gly Asn Val Tyr Leu Ala Arg Glu
                 85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125

Gln Ala His Leu His His Pro Asn Ile Leu Arg Leu Tyr Asn Tyr Phe
130                 135                 140

Tyr Asp Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
        195                 200                 205

Gly Leu Lys Gly Glu Leu Lys Ile Ala Asp Phe Gly Trp Ser Val His
    210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
        275                 280                 285

Asp Leu Lys Phe Pro Ala Ser Val Pro Thr Gly Ala Gln Asp Leu Ile
290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335

Pro Ser Ala Leu Gln Ser Val Ala
            340

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
cctgcaggtg gacctaaagt tc                                              22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
gcctgagcag tttggagatg ag                                              22

<210> SEQ ID NO 6
<211> LENGTH: 1224
<212> TYPE: DNA
<213> ORGANISM: Homo sapiens
```

<400> SEQUENCE: 6

```
ggccgggaga gtagcagtgc cttggacccc agctctcctc cccctttctc tctaaggatg      60
gcccagaagg agaactccta cccctggccc tacggccgac agacggctcc atctggcctg     120
agcaccctgc cccagcgagt cctccggaaa gagcctgtca ccccatctgc acttgtcctc     180
atgagccgct ccaatgtcca gcccacagct gcccctggcc agaaggtgat ggagaatagc     240
agtgggacac ccgacatctt aacgcggcac ttcacaattg atgactttga gattgggcgt     300
cctctgggca aaggcaagtt tggaaacgtg tacttggctc gggagaagaa aagccatttc     360
atcgtggcgc tcaaggtcct cttcaagtcc agatagaga aggagggcgt ggagcatcag     420
ctgcgcagag agatcgaaat ccaggcccac ctgcaccatc caacatcct gcgtctctac     480
aactattttt atgaccggag gaggatctac ttgattctag agtatgcccc ccgcggggag     540
ctctacaagg agctgcagaa gagctgcaca tttgacgagc agcgaacagc cacgatcatg     600
gaggagttgg cagatgctct aatgtactgc catgggaaga aggtgattca cagagacata     660
aagccagaaa atctgctctt agggctcaag ggagagctga agattgctga cttcggctgg     720
tctgtgcatg cgcccctcct gaggaggaag acaatgtgtg gcaccctgga ctacctgccc     780
ccagagatga ttgaggggcg catgcacaat gagaaggtgg atctgtggtg cattggagtg     840
ctttgctatg agctgctggt ggggaaccca ccctttgaga gtgcatcaca caacgagacc     900
tatcgccgca tcgtcaaggt ggacctaaag ttccccgctt ctgtgcccat gggagcccag     960
gacctcatct ccaaactgct caggcataac ccctcggaac ggctgcccct ggcccaggtc    1020
tcagcccacc cttgggtccg ggccaactct cggagggtgc tgcctccctc tgcccttcaa    1080
tctgtcgcct gatggtccct gtcattcact cgggtgcgtg tgtttgtatg tctgtgtatg    1140
tatagggaa agaagggatc cctaactgtt cccttatctg ttttctacct cctcctttgt    1200
ttaataaagg ctgaagcttt ttgt                                          1224
```

<210> SEQ ID NO 7
<211> LENGTH: 344
<212> TYPE: PRT
<213> ORGANISM: Homo sapiens

<400> SEQUENCE: 7

```
Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125

Gln Ala His Leu His His Pro Asn Ile Leu Arg Leu Tyr Asn Tyr Phe
    130                 135                 140
```

```
Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
        195                 200                 205

Gly Leu Lys Gly Glu Leu Lys Ile Ala Asp Phe Gly Trp Ser Val His
    210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
            245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
        275                 280                 285

Asp Leu Lys Phe Pro Ala Ser Val Pro Met Gly Ala Gln Asp Leu Ile
    290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335

Pro Ser Ala Leu Gln Ser Val Ala
            340

<210> SEQ ID NO 8
<211> LENGTH: 13
<212> TYPE: DNA
<213> ORGANISM: Artificial Sequence
<220> FEATURE:
<223> OTHER INFORMATION: Probe labeled on base 1

<400> SEQUENCE: 8
tcccgtgggc acg                                                    13

<210> SEQ ID NO 9
<211> LENGTH: 14
<212> TYPE: DNA
<213> ORGANISM: Artificial Sequence
<220> FEATURE:
<223> OTHER INFORMATION: Probe labeled on base 1

<400> SEQUENCE: 9
ctcccatggg cacg                                                   14
```

METHOD FOR THE DIAGNOSIS AND TREATMENT OF CARDIOVASCULAR DISEASES

The present invention refers to a method for the in vitro or in vivo diagnosis of cardiovascular diseases, in particular high blood pressure, stenosis, vessel occlusion and/or other thrombotic events, wherein the nucleotide at position 950 of a nucleic acid coding for the human ARK2 protein or the amino acid at position 298 of the human aurora 1 kinase (ARK2) protein of a sample of a person is determined as well as to the use of ARK2 for the development and/or production of a medicament for treating a cardiovascular disease.

The aurora kinases are an oncogenic family of mitotic serine/threonine kinases that are overexpressed in a number of solid tumors (Vankayalapati, H. et al. (2003) Molecular Cancer Therapeutics, 2, 283-294). Originally, a spontaneous chromosomal segregation defect mutant of Drosophila was identified and designated aurora (Shindo, M. et al. (1998), 244, 285-292). The human aurora 1 kinase is also known as AUR1, ARK2, AIk2, AIM-1 and STK12. Herein the term ARK2 is used. ARK2 shall play a role in mitosis, specifically it accumulates in the midbodies during mitosis (Shindo, M. et al. (1998), supra). ARK2 deficient cells have also been shown to exhibit cytokinesis defects (Descamps & Prigent (2001), Sci. STKE, 173, 1). The gene of ARK2 is located on chromosome 17p13.1.

In order to better understand a potential involvement of ARK2 in the occurrence and progression of human diseases, genotype-phenotype association analyses have been carried out with a well characterized patient group with respect to a C→T variation at position 950 of the ARK2 reference sequence published under the reference number NM_004217. Said variation leads to an amino acid change from threonine to methionine (Thr→Met) at the corresponding position 298 in the ARK2 protein. Different genetic variants of the ARK2 gene are already known as SNPs (single nucleotide polymorphisms) and published under Surprisingly it has been found that in particular the variation at position 950 from cytosine to thymidine in a nucleic acid coding for the human ARK2 protein or the corresponding variation of the ARK2 protein at position 298 from threonine to methionine correlates with the occurrence of cardiovascular diseases.

Therefore, a subject matter of the present invention relates to an in vitro or in vivo diagnosis of cardiovascular diseases, wherein the nucleotide at position 950 of a nucleic acid coding for the human ARK2 protein or the amino acid at position 289 of the human ARK2 protein of a sample of a person or patient is determined.

In a preferred embodiment of the present invention the cardiovascular disease is high blood pressure, stenosis, vessel occlusion and/or other thrombotic events.

In particular, if the nucleotide at position 950 is determined as thymidine in the chromosomal DNA or uracile in the mRNA or the amino acid at position 298 is determined as methionine there exists a higher risk of high blood pressure and/or stenosis.

According to the present invention, the term "ARK2-C950C" refers to the group of persons which have cytidine on both alleles of the gene coding for ARK2 at position 950 of the reference sequence NM_004217 which leads to the amino acid threonine at position 298 of the corresponding protein. These persons are homozygous with respect to this ARK2 variant. Consequently, the term "ARK2-C950T" refers to the group of persons who have cytidine on one allele of the gene coding for ARK2 which leads to threonine at position 298 of the corresponding protein and thymidine on the other allele of the gene coding for ARK2 which leads to methionine at position 298 of the corresponding protein. These persons are heterozygous with respect to this ARK2 variant. According to the present invention, the term "ARK2-T950T" refers to the group of persons which have thymidine on both alleles of the gene coding for ARK2 at position 950 of the reference sequence NM_004217 which leads to the amino acid methionine at position 298 of the corresponding protein. These persons are homozygous with respect to this ARK2 variant.

The nucleic acid sequence of the reference sequence coding for the human ARK2 protein preferably has the nucleic acid sequence of SEQ ID NO: 1 and the amino acid sequence of the human ARK2 protein preferably has the amino acid sequence of SEQ ID NO: 3. However, the present invention encompasses also other variants of human ARK2 and the non-human homologs thereof, as for example other mammalian ARK2 homologs or the ARK2 homologs from Drosophila, *Caenorhabdidis elegans*, mouse or rat, provided that there is a nucleotide exchange from cytidine to thymidine at the position corresponding to position 950 of said reference sequence and/or an amino acid exchange from threonine to methionine at the position corresponding to position 298 of said reference sequence and further provided that the corresponding protein has a serine threonine kinase activity. Said enzyme activity can be measured by kinase assays known to a person skilled in the art and/or as described in the present specification.

Generally, the specific nucleotide at position 950 can be determined by a nucleic acid sequencing method, a mass spectrometric analysis of the nucleic acid, a hybridisation method and/or an amplification method. Examples of a nucleic acid sequencing method are pyrosequencing and/or sequencing with the help of radioactive and/or fluorescence labelled nucleotides. Examples of the hybridisation method are Southern blot analysis, Northern blot analysis and/or a hybridisation method on a DNA-microarray. Examples of an amplification method are a TaqMan analysis, a differential RNA display analysis and/or a representational difference analysis (Shi M. M. (2002) Am J Pharmacogenomics, 2(3), 197-205; Kozian & Kirschbaum (1999) Trends Biotechnol, 17(2), 73-8.)

Furthermore, the amino acid sequence at position 298 can be determined by a method measuring the amount of the specific protein and/or a method measuring the activity of the specific protein. Examples of a method for measuring the amount of the specific protein are a Western blot analysis and/or an ELISA. Examples for measuring the activity of the specific protein are an in vitro test assay and/or an in vitro whole cell test assay with human cells, animal cells, bacterial cells or yeast cells, all known to a person skilled in the art and/or described in the present application.

Examples of a sample for the detection of the respective variant are a cell, a tissue or a body fluid, in particular in cellular components of the blood, endothelial cells or smooth muscle cells. Preferably the sample is pre-treated by conventional methods known to a person skilled in the art in order to isolate and/or purify the nucleic acids or chromosomal DNA, or the proteins of the sample for the further analysis.

In an optional further step the risk of a person to suffer from a cardiovascular disease can be determined as shown in the examples.

In another optional further step an appropriate pharmaceutical is selected or the dosage of a pharmaceutical is determined.

In general, the found genetic variation in the ARK2 gene can be used in accordance with the present invention as a genetic marker for the risk assessment, the genetic characterization or classification of a person and/or the prophylactic treatment of a cardiovascular disease (also known as "coronary heart disease"), in particular of high blood pressure, stenosis, vessel occlusion and/or other thrombotic events.

Furthermore, the genetic variation can be used in accordance with the present invention as a genetic marker for the adaptation of the dosage or generally of increasing the effectiveness of an effective therapeutic agent for the treatment of a person or patient (hereinafter also referred to as "individual") and/or for the identification of individuals being under or selected to be under clinical trial studies with an increased risk for cardiovascular disease, in particular of high blood pressure and/or stenosis. The genetic variation can also be used in accordance with the present invention for the evaluation of the tolerance, safety and efficacy of a pharmaceutically active substance for a specific individual or for identifying the individual suitable for a particular treatment of said diseases.

The present invention can also be used to identify risk factors for said diseases for each individual to be treated or advised.

In general, suitable individuals are (i) individuals who do not exhibit the symptoms of a cardiovascular disease, (ii) individuals in whom the risk of developing a cardiovascular disease has already been detected but who do not yet exhibit the symptoms of the disease, and (iii) individuals who have previously been diagnosed as suffering from a cardiovascular disease.

A preferred method for the diagnosis of a cardiovascular disease in accordance with the present invention contains the following steps:
(a) optionally obtaining a sample, in particular a cell, tissue, body fluid, a cellular component of the blood, endothelial cells or smooth muscle cells, from a person or patient that should be investigated;
(b) isolating a nucleic acid probe, in particular a DNA probe from the sample;
(c) amplifying the specific region encompassing position 950 of the ARK2 gene with the help of primers, in particular the primers as specified in the Examples;
(d) sequencing the amplified region;
(e) analysing the sequenced region; and
(f) assessing the risk for a cardiovascular disease, in particular for high blood pressure, stenosis, vessel occlusion and/or other thrombotic events.

An alternative method for the diagnosis of a cardiovascular disease in accordance with the present invention contains the following steps:
(a) optionally obtaining a sample, in particular a cell, tissue, body fluid, a cellular component of the blood, endothelial cells or smooth muscle cells, from a person or patient that should be investigated;
(b) isolating the ARK2 protein from the sample;
(c) determining the amino acid at position 298 of the ARK2 protein; and
(d) assessing the risk for a cardiovascular disease, in particular for high blood pressure, stenosis, vessel occlusion and/or other thrombotic events.

The present invention generally refers also to a method for determining the risk of a person to suffer from a cardiovascular disease, wherein the method comprises the steps of
(a) determining the genotype of the ARK2 gene of a person in vitro or in vivo, and
(b) converting the data obtained in (a) in order to give a prognosis for said person's risk of developing a cardiovascular disease,
whereas the detection of an ARK2 Met298Met variation is an indicator for an increased risk for developing a cardiovascular disease, in particular high blood pressure, stenosis, vessel occlusion and/or other thrombotic events.

Another embodiment of the present invention generally refers to a method for selecting a pharmaceutically active compound or determining the dosage of a pharmaceutically active compound for a person suffering from a cardiovascular disease, in particular high blood pressure, stenosis, vessel occlusion and/or other thrombotic events, or for determining the effectiveness of a therapeutic treatment of a cardiovascular disease, in particular high blood pressure, stenosis, vessel occlusion and/or other thrombotic events,
wherein the method comprises the steps of
(a) determining the genotype of the ARK2 gene of a person in vitro, and
(b) selecting a pharmaceutically active compound or determining the dosage of a pharmaceutically active compound for said person or determining the effectiveness of a therapeutic treatment,
whereas the pharmaceutically active compound is selected and/or the dosage of a pharmaceutically active compound and/or the effectiveness of a therapeutic treatment is determined for a person having an ARK2 Met298Met variation.

Still another embodiment of the present invention generally refers to a method for identifying a person having an increased risk for a cardiovascular disease, wherein the method comprises the steps of
(a) determining the genotype of the ARK2 gene of a person in vitro or in vivo, and
(b) converting the data obtained in (a) in order to identify the person,
whereas the detection of an ARK2 Met298Met variation is an indicator for an increased risk for developing a cardiovascular disease, in particular high blood pressure, stenosis, vessel occlusion and/or other thrombotic events.

The determination of the genotype of the ARK2 gene can be carried out by any method known to a person skilled in the art, in particular by any method described herein.

In addition, ARK2 and/or the ARK2 variants as described herein can be used in accordance with the present invention for the production of a medicament for treating a cardiovascular disease. Therefore, an additional embodiment of the present invention refers to the use of an ARK2 protein containing an amino acid sequence according to SEQ ID NO: 3 or of an ARK2 variant at the amino acid position 298 and/or the corresponding nucleic acid sequence coding for the ARK2 protein or variant thereof for the production of a medicament for treating a cardiovascular disease, in particular high blood pressure, stenosis, vessel occlusion and/or other thrombotic events. In particular, the variant is a Met298Met variant of the ARK2 protein according to SEQ ID NO: 7 or a T950T variant of the ARK2 nucleic acid according to SEQ ID NO: 6. In particular, kinase assays known to those of skill in the art and/or as described herein can be used to identify modulators, e.g. activators or inhibitors, of the ARK2 protein and/or the ARK2 variant, in particular the ARK2-Met298Met variant.

Consequently, ARK2 and/or the ARK2 variants described herein can also be used in accordance with the present invention as part of a high throughput-screening assay for the detection and evaluation of pharmaceutically active compounds for the treatment of said diseases. Therefore, an additional embodiment of the present invention refers to a method of screening a pharmaceutically active agent for the treatment of a cardiovascular disease, wherein the method comprises the steps of:
(a) providing an ARK2 protein containing an amino acid sequence according to SEQ ID NO: 3 or an ARK2 variant at the amino acid position 298 and/or the corresponding nucleic acid coding for the ARK2 protein or variant thereof,
(b) providing a test compound,
(c) measuring or detecting the influence of the test compound on the ARK2 protein or ARK2 variant or on the corresponding nucleic acid, and
(d) isolating a compound suitable for the treatment of a cardiovascular disease, in particular high blood pressure, stenosis, vessel occlusion and/or other thrombotic events.

In particular, the variant is a Met298Met variant of the ARK2 protein according to SEQ ID NO: 7 or a T950T variant of the ARK2 nucleic acid according to SEQ ID NO: 6. In general, the ARK2 protein, the ARK2 variant or the nucleic acid coding for the ARK2 protein or variant is provided e.g. in an assay system and brought directly or indirectly into contact with a test compound, in particular a biochemical or chemical test compound, e.g. in the form of a chemical compound library. Then, the influence of the test compound on the ARK2 protein or the nucleic acid coding for the ARK2 protein is measured or detected. Thereafter, suitable modulators, e.g. activators or inhibitors, can be analyzed and/or isolated. For the screening of chemical compound libraries, the use of high-throughput assays are preferred which are known to the skilled person or which are commercially available.

In general, the influence of the test compound on the ARK2 protein or the ARK2 variant or the nucleic acid coding for the ARK2 protein or the variant may be any physical, chemical or phenotypic effect of the compound upon the protein or nucleic acid or upon a cell comprising the protein or nucleic acid, thereby identifying a compound that modulates the protein or nucleic acid. In the present case it is preferable to measure or detect the influence of the test compound on the kinase activity of the ARK2 protein or the ARK2 variant as described herein.

The general concept of a kinase assay is that the kinase to be analysed, here the ARK2 serine/threonine kinase, is brought into contact with a suitable substrate or peptide containing a serine or threonine residue which can be phosphorylated by the kinase in the presence of preferably ATP in a suitable buffer. Preferably the substrate is a dye-labelled substrate, e.g. a fluorescent dye-labelled peptide, e.g. a fluorescein-labelled peptide. Serine/Threonine kinase assays are commercially available, e.g. the HitHunter™ Serine/Threonine Kinase Assay from Applied Biosystems, Inc., California, USA or the IQ™ Serine/Threonine Kinase Assay from Pierce Biotechnology, Inc., Illinois, USA. Other kinase assays are further described in detail below.

According to the present invention the term "chemical compound library" refers to a plurality of chemical compounds that have been assembled from any of multiple sources, including chemically synthesized molecules and natural products, or that have been generated by combinatorial chemistry techniques.

In general, the influence of the test compound on ARK2, the ARK2 variant or the nucleic acid coding for ARK2 protein or variant is measured or detected in a heterogeneous or homogeneous assay. As used herein, a heterogeneous assay is an assay which includes one or more washing steps, whereas in a homogeneous assay such washing steps are not necessary. The reagents and compounds are only mixed and measured.

Suitable functional assays may be based on the gene expression of ARK2 or its serine/threonine kinase activity. In general, commercially available kinase assays systems quantitatively detect the amount of phosphate incorporated in a substrate.

Heterogeneous assays are, for example, ELISA, DELFIA, SPA and flashplate assays.

ELISA (enzyme linked immuno sorbent assay)-based assays are offered by various companies. The assays employ random peptides that can be phosphorylated by a kinase, such as ARK2. Kinase-containing samples are usually diluted into a reaction buffer containing e.g. ATP and requisite cations and then added to plate wells. Reactions are stopped by simply removing the mixtures. Thereafter, the plates are washed. The reaction is initiated e.g. by the addition of a biotinylated substrate to the kinase. After the reaction, a specific antibody is added. The samples are usually transferred to pre-blocked protein-G plates and after washing e.g. streptavidin-HRP is added. Thereafter, unbound streptavidin-HRP (horseradish peroxidase) is removed, the peroxidase colour reaction is initiated by addition of the peroxidase substrate and the optical density is measured in a suitable densitometer.

DELFIA (dissociation enhanced lanthanide fluoro immuno assay)-based assays are solid phase assay. The antibody is usually labelled with Europium or another lanthanide and the Europium fluorescence is detected after having washed away un-bound Europium-labelled antibodies.

SPA (scintillation proximity assay) and the flashplate assay usually exploit biotin/avidin interactions for capturing radiolabelled substrates. Generally the reaction mixture includes the kinase, a biotinylated peptide substrate and $\gamma$-$[P^{33}]$ATP. After the reaction, the biotinylated peptides are captured by streptavidin. In the SPA detection, streptavidin is bound on scintillant containing beads whereas in the flashplate detection, streptavidin is bound to the interior of the well of scintillant containing microplates. Once immobilized, the radiolabelled substrate is close enough to the scintillant to stimulate the emission of light.

Alternative homogeneous assays are, for example, TR-FRET, FP, ALPHA and gene assays.

TR-FRET (time-resolved fluorescence resonance energy transfer)-based assays are assays which usually exploit the fluorescence resonance energy transfer between Europium and APC, a modified allophycocyanin or other dyes with overlapping spectra such as Cy3/Cy5 or Cy5/Cy7 (Schobel, U. et al. (1999) Bioconjugate Chem. 10, 1107-1114). After excitation e.g. of Europium with light at 337 nm, the molecule fluoresces at 620 nm. But if this fluorophore is close enough to APC, the Europium will transfer its excitation energy to APC, which fluoresces at 665 nm. The kinase substrate is usually a biotin-labelled substrate. After the kinase reaction, Europium-labelled-(P)-specific antibodies are added along with streptavidin-APC. The phosphorylated peptides bring the Europium-labelled antibody and the streptavidin-APC into close contact. The close proximity of the APC to the Europium fluorophore will cause a quenching of the Europium fluorescence at benefit of the APC fluorescence (FRET).

Fluorescence polarisation (FP)-based assays are assays which use polarized light to excite fluorescent substrate peptides in solution. These fluorescent peptides are free in solution and tumble, causing the emitted light to become depolarised. When the substrate peptide binds to a larger molecule, however, such as (P)-Tyr, its tumbling rates are greatly decreased, and the emitted light remains highly polarized. For a kinase assay there are generally two options:

(a) A fluorescent phosphopeptide tracer is bound to a (P)-specific antibody. Phosphorylated products will compete the fluorescent phosphopeptide from the antibody resulting in a change of the polarisation from high to low.
(b) A phosphorylated substrate peptide binds to the phospho-specific antibody resulting in a change of polarisation from low to high.

ALPHA (amplified luminescent proximity homogenous)-based assays, are assays which rely on the transfer of singlet oxygen between donor and acceptor beads brought into proximity by a phosphorylated peptide. Upon excitation at 680 nm, photosensitisers in donor beads convert ambient oxygen to singlet-state oxygen, which diffuses up to a distance of 200 nm. Chemiluminescent groups in the acceptor beads transfer energy to fluorescent acceptors within the bead, which then emits light at approximately 600 nm.

EFC (enzyme fragment complementation)-based assays or equivalent assays can be used in particular for high-throughput screening of compounds. The EFC assay is based on an engineered β-galactosidase enzyme that consists of two fragments—the enzyme acceptor (EA) and the enzyme donor (ED). When the fragments are separated, there is no β-galactosidase activity, but when the fragments are together they associate (complement) to form active enzyme. The EFC assay utilizes an ED-analyte conjugate in which the analyte may be recognized by a specific binding protein, such as an antibody or receptor. In the absence of the specific binding protein, the ED-analyte conjugate is capable of complementing EA to form active β-galactosidase, producing a positive luminescent signal. If the ED-analyte conjugate is bound by a specific binding protein, complementation with EA is prevented, and there is no signal. If free analyte is provided (in a sample), it will compete with the ED-analyte conjugate for binding to the specific binding protein. Free analyte will release ED-analyte conjugate for complementation with EA, producing a signal dependent upon the amount of free analyte present in the sample.

Another example of a gene assay is a functional assay wherein the activity of the kinase is converted into a functional cellular response such as growth, growth arrest, differentiation or apoptosis. For this type of screening yeast is a particularly suitable model system. For example in an ARK2-yeast functional assay, when cultured on glucose containing medium, the e.g. ARK2-yeast cells grow like normal yeast cells. When, however being exposed to galactose, the intracellular expression of ARK2 is induced causing the yeast cell to die. Compounds that inhibit ARK2 activity prevent the cell death in this case.

Another assay is based on solid phase-bound polypeptides such as ARK2 and the interference with the compounds to be tested. Thus, a test compound contains a detectable marker, for example, the compound can be radioactively labelled, fluorescence-labelled or luminescence-labelled as already explained above. Furthermore, compounds can be coupled to proteins which permit indirect detection, for example by means of enzymatic catalysis employing a peroxidase assay which uses a chromogenic substrate or by means of binding a detectable antibody. Another possibility is that of investigating the solid phase-bound protein complexes by means of mass spectrometry (SELDI). Changes in the conformation of e.g. ARK2 or the ARK2 variants described herein as the result of interaction with a test substance can be detected, for example, by the change in the fluorescence of an endogenous tryptophan residue in the polypeptide.

The solid phase-bound polypeptides can also be part of an array. Methods for preparing such arrays using solid phase chemistry and photolabile protecting groups are disclosed, for example, in U.S. Pat. No. 5,744,305. These arrays can also be brought into contact with test compound or compound libraries and tested for interaction, for example binding or changing conformation. Suitable formats of the arrays are currently in the 96-, 384- or 1,536 formats for both the primary and secondary screens.

In another embodiment of the present invention, the method is carried out using whole cells. Usually cells growing at the bottom of multiwell plates are fixed and permeabilized, blocked and incubated with e.g. a primary (P)-specific antibody against the substrate of interest. Then, e.g. Europium labelled or HRP conjugated secondary antibodies in conjunction with specific chemiluminescent or colorimetric substances, e.g. as described above, are utilized to generate the signal. In combination with the use of a microscope not only the amount of (P)-specific antibodies can be quantified on the single cell level, but also phosphorylation-induced translocations of a substrate or morphological changes of the cells.

Advantageously the method of the present invention is carried out in a robotics system e.g. including robotic plating and a robotic liquid transfer system, e.g. using microfluidics, i.e. channeled structured.

In another embodiment of the present invention, the method is carried out in form of a high-through put screening system. In such a system advantageously the screening method is automated and miniaturized, in particular it uses miniaturized wells and microfluidics controlled by a roboter.

In view of the above subject matter the present invention refers also to a method for producing a medicament for the treatment of a cardiovascular disease, in particular high blood pressure, stenosis, vessel occlusion and/or other thrombotic events, wherein the method comprises the steps of:
(a) carrying out the screening method as explained above, and
(b) formulating the isolated compound with one or more pharmaceutically acceptable carriers or auxiliary substances.

According to step (b) of the above method the detected test compound is usually formulated with one or more pharmaceutically acceptable additives or auxiliary substances, such as physiological buffer solution, e.g. sodium chloride solution, demineralized water, stabilizers, ε-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the medicament is in general adjusted using a suitable organic or inorganic buffer, such as, for example, preferably using a phosphate buffer, tris buffer (tris (hydroxymethyl)aminomethane), H EPES buffer ([4-(2-hydroxyethyl)piperazino]-ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The medicament can be administered in a conventional manner, e.g. by means of oral dosage forms, such as, for example, tablets or capsules, by means of the mucous membranes, for example the nose or the oral cavity, in the form of dispositories implanted under the skin, by means of injections, infusions or gels which contain the medicaments according to the invention. Furthermore, the treatment can be carried out by means of a transdermal therapeutic system (TTS), which makes possible a temporally controlled release of the medicaments. TTS are known for example, from EP 0 944 398 A1, EP 0 916 336 A1, EP 0 889 723 A1 or EP 0 852 493 A1.

Injection solutions are in general used if only relatively small amounts of a solution or suspension, for example about 1 to about 20 ml, are to be administered to the body. Infusion solutions are in general used if a larger amount of a solution or suspension, for example one or more litres, are to be administered. Since, in contrast to the infusion solution, only a few millilitres are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

More preferred steps are individually or collectively specified in the Examples and are incorporated hereby by reference to each step.

The following Figures, Tables, Sequences and Examples shall explain the present invention without limiting the scope of the invention.

BRIEF DESCRIPTION OF THE DRAWINGS

FIG. 1A shows the nucleic acid sequence (SEQ ID NO:1) of the human ARK2 gene with the NCBI number NM_004217.

FIG. 1B shows part of the chromosomal nucleic acid sequence of ARK2 with the number AC135178. The primers used for amplification of the genetic section with the genetic variation C→T corresponding to position 950 of reference sequence NM_004217 are marked in bold face and underlined

```
(ARK2-298R = CCTGCAGGTGGACCTAAAGTTC (SEQ ID NO:
  4);
ARK2-298F = GCCTGAGCAGTTTGGAGATGAG) (SEQ ID NO:
  5)).
```

FIG. 2 shows the amino acid sequence (SEQ ID NO:3) of the human ARK2 derived from the nucleic acid sequence with the NCBI number NM_004217. The amino acid position 298 in the ARK2 protein is in bold face and underlined (SEQ ID NO:3).

FIG. 3 shows the nucleic acid sequence of the human ARK2 gene T950T variant (SEQ ID NO:6).

FIG. 4 shows the amino acid sequence of the human ARK2 Met298Met variant (SEQ ID NO:7).

DESCRIPTION OF THE SEQUENCES

SEQ ID NO: 1 shows the nucleic acid sequence of the human ARK2 protein with the NCBI number NM_004217.

SEQ ID NO: 2 shows part of the chromosomal nucleic acid sequence of ARK2 with the number AC135178.

SEQ ID NO: 3 shows the amino acid sequence of the human ARK2 derived from the nucleic acid sequence with the NCBI number NM_004217.

SEQ ID NO: 4 shows the first primer sequence ARK2-298R.

SEQ ID NO: 5 shows the second primer sequence ARK2-298F of the complementary sequence.

SEQ ID NO: 6 shows the nucleic acid sequence of the human ARK2 gene T950T variant.

SEQ ID NO: 7 shows the amino acid sequence of the human ARK2 Met298Met variant.

EXAMPLES

SNP Detection by 5'-Nuclease Assays (Taqman™)

Oligonucleotides (Primers) for Amplification:

The following primers were used for the detection of the nucleotide exchange from C to T at position 950 in the ARK2 sequence with the reference number NM_004217:

Primer 1: 5'-GCCTGAGCAGTTTGGAGATGAG-3' (nucleotides 179605-179584 of the reference sequence AC135178; FIG. 1B; SEQ ID NO: 5);

Primer 2: 5'-CCTGCAGGTGGACCTAAAGTTC-3' (complementary sequence of bases 179532-179553 of the reference sequence AC135178; FIG. 1B; SEQ ID NO: 4).

PCR Protocol for Amplification:

The reagents used were from Applied Biosystems (Foster City, USA). The PCR reaction was carried out in a Primus 96 plus thermal cycler (MWG Biotech AG, Germany) in a total volume of 5 µl with 2.5 µl SuperHot-Master-Mix (Bioron GmbH, Germany), 0.125 µl Assay-by-Design-Mix (Applied Biosystems, Austria), 0.375 µl $H_2O$ and 2 µl DNA. The reaction mixtures were overlaid by 15 µl mineral oil.

Amplification Program of the PCR Reactions:

94° C. for 1 min×1 cycle

92° C. for 15 sec×45 cycles

60° C. for 1 min×1 cycle;

Analysis of the PCR Products

The fluorescence was detected in a VICTOR Fluorescence Plate Reader (HVD Life Sciences, Austria) with an excitation/emission filter of 485 nm/520 nm for FAM-marked probes (298Thr allele; ARK2-298M1 (Thr) FAM-TC-CCGTGGGCACG (SEQ ID NO:8)) and 530 nm/572 nm for VIC-marked probes (298Met allele; ARK2-298V1 (Met) VIC-CTCCCATGGGCACG (SEQ ID NO:8)). The data were exported in a MS-Excel format and analysed with scatter plots.

Results

Characteristics of the Group of Persons

Table 1 shows the characteristics of the group of persons studied.

TABLE 1

|  |  | n | % |
|---|---|---|---|
| Total |  | 2074 |  |
| Sex | Female | 603 | 29.07 |
|  | Male | 1471 | 70.93 |
| Age |  | 61.8 (+/−10.5) |  |
| BMI (Body Mass Index) |  | 29.1 (+/−4.4) |  |

TABLE 1-continued

|  | n | % |
|---|---|---|
| Blood Pressure | 1214 | 58.7 |
| Smoker | 1372 | 66.41 |
| Type II Diabetes | 361 | 17.46 |
| Myocardial infarction | 830 | 40.59 |
| Stroke | 145 | 7.01 |

Frequence and Distribution of the Variants of the ARK2 Gene

Table 2 shows the frequency and distribution of the genetic variants of the ARK2 gene at position 950 of the reference sequence NM_004217 in the patient group studied.

TABLE 2

|  | Frequency | Percentage |
|---|---|---|
| ARK2-T950T (ARK2 Met298Met) | 21 | 1.46 |
| ARK2-C950T (ARK2 Thr298Met) | 290 | 20.18 |
| ARK2-C950C ARK2 Thr298Thr) | 1126 | 78.36 |

Influence of the Variant Thr298Met of ARK2

Table 3 shows the influence of the variant Thr298Met of ARK2 on the occurrence of high blood pressure, coronary heart diseases (with a stenosis of >20%), the incidence of more than one myocardial infarction and stroke/TIA/PRIND (TIA=transitoric ischemic attack; PRIND=prolonged reversible ischemic neurological deficit) in the patient group studied. P-values less than 0.05 are considered to be statistically relevant.

TABLE 3

|  | ARK2-T950T Met298Met | ARK2-C950T Thr298Met | ARK2-C950C Thr298Thr | p value | P value adjusted |
|---|---|---|---|---|---|
| High blood pressure | 16 (76.19%) | 184 (63.45%) | 618 (54.88%) | 0.0063 |  |
| Coronary heart diseases | 17 (85.00%) | 238 (82.93%) | 859 (77.81%) |  | 0.0286 |
| >1 Myocardial infarction | 3 (14.29%) | 28 (9.66%) | 66 (5.86%) | 0.0464 |  |
| Stroke/TIA/PRIND | 6 (28.57%) | 17 (5.86%) | 83 (7.37%) | 0.0006 |  |

Results:

The patients with ARK2-T950T showed a statistically higher incidence for high blood pressure and coronary heart diseases, the incidence of more than one myocardial infarction and stroke/TIA/PRIND compared to patients with different ARK2 genotype at this position 950.

Conclusion:

The statistically significant associations between the genetic variants of the gene coding for ARK2 and/or the protein ARK2 shown above are a clear indication for the involvement of said genetic variants in the occurrence of cardiovascular diseases, in particular high blood pressure, stenosis, vessel occlusion and/or thrombotic events. Consequently, said genetic variants are biological markers for e.g. the prognosis of cardiovascular diseases, in particular high blood pressure, stenosis, vessel occlusion and/or thrombotic events). Further embodiments of the invention based on the present finding are described in further details in the present specification.

```
SEQ ID NO: 1
  1 ggccgggaga gtagcagtgc cttggac-
    ccc agctctcctc cccctttctc tctaaggatg
 61 gcccagaagg agaactccta ccctggc-
    cc tacggccgac agacggctcc atctggcctg
121 agcaccctgc cccagcgagt cctccg-
    gaaa gagcctgtca ccccatctgc acttgtcctc
181 atgagccgct ccaatgtcca gccca-
    cagct gcccctggcc agaaggtgat ggagaatagc
241 agtgggacac ccgacatctt aacgcg-
    gcac ttcacaattg atgactttga gattgggcgt
301 cctctgggca aaggcaagtt tg-
    gaaacgtg tacttggctc gggagaagaa aagccatttc
```

-continued

```
  361 atcgtggcgc tcaaggtcct ct-
      tcaagtcc cagatagaga aggagggcgt ggagcatcag 421 ctgcgcagag agatcgaaat ccaggc-
      ccac ctgcaccatc caacatcct gcgtctctac 481 aactattttt atgaccggag gaggatc-
      tac ttgattctag agtatgcccc ccgcggggag 541 ctctacaagg agctgcagaa gagctgca-
      ca tttgacgagc agcaacagc cacgatcatg 601 gaggagttgg cagatgctct aatgtact-
      gc catgggaaga aggtgattca cagagacata 661 aagccagaaa atctgctctt agggct-
      caag ggagagctga agattgctga cttcggctgg 721 tctgtgcatg cgccctccct gaggag-
      gaag acaatgtgtg gcaccctgga ctacctgccc 781 ccagagatga ttgaggggcg catgca-
      caat gagaaggtgg atctgtggtg cattggagtg 841 ctttgctatg agctgctggt gggaac-
      cca cccttcgaga gtgcatcaca aacgagacc 901 tatcgccgca tcgtcaaggt ggac-
      ctaaag ttccccgctt ctgtgcccac gggagcccag 961 gacctcatct ccaaactgct caggcat-
      aac ccctcggaac ggctgccct ggcccaggtc 1021 tcagcccacc cttgggtccg ggc-
      caactct cggagggtgc tgcctccctc tgcccttcaa 1081 tctgtcgcct gatggtccct gtcat-
      tcact cgggtgcgtg tgtttgtatg tctgtgtatg 1141 tataggggaa agaagggatc cctaact-
      gtt cccttatctg ttttctacct cctcctttgt 1201 ttaataaagg ctgaagcttt ttgt SEQ ID NO: 2
179461 TCCAAACAGA ATGGGTAGTC AAGGAA-
       GATG TAGCCAGGGT GAAACTAATG CAGCCCTTCC 179521 ATCTCTTCAC ACCTGCAGGT GGAC-
       CTAAAG TTCCCCGCTT CCGTGCCCAT GGGAGCCCAG 179581 GACCTCATCT CCAAACTGCT CAGGCAT-
       AAC CCCTCGGAAC GGCTGCCCCT GGCCCAGGTC 179641 TCAGCCCACC CTTGGGTCCG GGC-
       CAACTCT CGGAGGGTGC TGCCTCCCTC TGCCCTTCAA

SEQ ID NO: 3
MAQKENSYPWPYGRQTAPSGLSTLPQRVLRKEPVTPSALVLMSRSNVQPTAAPGQKVMENSSGT

PDILTRHFTIDDFEIGRPLGKGKFGNVYLAREKKSHFIVALKVLFKSQIEKEGVEHQLRREIEI

QAHLHHPNILRLYNYFYDRRRIYLILEYAPRGELYKELQKSCTFDEQRTATIMEELADALMYCH

GKKVIHRDIKPENLLLGLKGELKIADFGWSVHAPSLRRKTMCGTLDYLPPEMIEGRMHNEKVDL

WCIGVLCYELLVGNPPFESASHNETYRRIVKVDLKFPASVPTGAQDLISKLLRHNPSERLPLAQ

VSAHPWVRANSRRVLPPSALQSVA

SEQ ID NO: 4
    1 CCTGCAGGTGGACCTAAAGTTC

SEQ ID NO: 5
    1 GCCTGAGCAGTTTGGAGATGAG
SEQ ID NO: 6
    1 ggccgggaga gtagcagtgc cttggac-
      ccc agctctcctc cccctttctc tctaaggatg 61 gcccagaagg agaactccta cccctggc-
      cc tacggccgac agacggctcc atctggcctg 121 agcaccctgc ccagcgagt cctccg-
      gaaa gagcctgtca ccccatctgc acttgtcctc
```

-continued

```
  181  atgagccgct ccaatgtcca gccca-
       cagct gccccctggcc agaaggtgat ggagaatagc 241  agtgggacac ccgacatctt aacgcg-
       gcac ttcacaattg atgactttga gattgggcgt 301  cctctgggca aaggcaagtt tg-
       gaaacgtg tacttggctc gggagaagaa aagccatttc 361  atcgtggcgc tcaaggtcct ct-
       tcaagtcc cagatagaga aggagggcgt ggagcatcag 421  ctgcgcagag agatcgaaat ccaggc-
       ccac ctgcaccatc caacatcct gcgtctctac 481  aactattttt atgaccggag gaggatc-
       tac ttgattctag agtatgcccc ccgcggggag 541  ctctacaagg agctgcagaa gagctgca-
       ca tttgacgagc agcgaacagc cacgatcatg 601  gaggagttgg cagatgctct aatgtact-
       gc catgggaaga aggtgattca cagagacata 661  aagccagaaa atctgctctt agggct-
       caag ggagagctga agattgctga cttcggctgg 721  tctgtgcatg cgccctccct gaggag-
       gaag acaatgtgtg cacccctgga ctacctgccc 781  ccagagatga ttgaggggcg catgca-
       caat gagaaggtgg atctgtggtg cattggagtg 841  ctttgctatg agctgctggt ggggaac-
       cca ccctttgaga gtgcatcaca aacgagacc 901  tatcgccgca tcgtcaaggt ggac-
       ctaaag ttccccgctt ctgtgcccat gggagcccag 961  gacctcatct ccaaactgct caggcat-
       aac ccctcggaac ggctgcccct ggcccaggtc 1021  tcagcccacc cttgggtccg ggc-
       caactct cggagggtgc tgcctccctc tgcccttcaa 1081  tctgtcgcct gatggtccct gtcat-
       tcact cgggtgcgtg tgtttgtatg tctgtgtatg 1141  tataggggaa agaagggatc cctaact-
       gtt cccttatctg ttttctacct cctcctttgt 1201  ttaataaagg ctgaagcttt ttgt
```

SEQ ID NO: 7
MAQKENSYPWPYGRQTAPSGLSTLPQRVLRKEPVTPSALVLMSRSNVQPTAAPGQKVMENSSGT

PDILTRHFTIDDFEIGRPLGKGKFGNVYLAREKKSHFIVALKVLFKSQIEKEGVEHQLRREIEI

QAHLHHPNILRLYNYFYDRRRIYLILEYAPRGELYKELQKSCTFDEQRTATIMEELADALMYCH

GKKVIHRDIKPENLLLGLKGELKIADFGWSVHAPSLRRKTMCGTLDYLPPEMIEGRMHNEKVDL

WCIGVLCYELLVGNPPFESASHNETYRRIVKVDLKFPASVPMGAQDLISKLLRHNPSERLPLAQ

VSAHPWVRANSRRVLPPSALQSVA

---

We claim:

1. A method for determining an increased risk of occurrence of a cardiovascular disease in a human subject, said method comprising:

(a) obtaining a sample from said subject, said sample including a nucleic acid comprising a portion of the human aurora 1 kinase (ARK2) gene comprising the position corresponding to position 950 of SEQ ID NO: 6; and (b) detecting in said nucleic acid the presence of a T at the position corresponding to position 950 of SEQ ID NO: 6 in both alleles of the ARK2 gene;

wherein the presence of a T at the position corresponding to position 950 of SEQ ID NO: 6 in both alleles of the ARK2 gene is indicative of increased risk for a cardiovascular disease.

2. The method of claim 1 wherein the cardiovascular disease is selected from the group consisting of: high blood pressure, stenosis, vessel occlusion and thrombotic events.

3. The method according to claim 1 wherein said comprises the nucleotide sequence of SEQ ID NO: 6.

4. The method according to claim 1 wherein the nucleotide at position 950 is determined by a method selected from the group consisting of: a nucleic acid sequencing method, a mass spectrometric analysis of the nucleic acid, a hybridization method and an amplification method.

5. The method according to claim 4, wherein said nucleic acid sequencing method is selected from the group consisting of: pyrosequencing and sequencing using radioactive and fluorescence labeled nucleotides.

6. The method according to claim 4 wherein said hybridization method is selected from the group consisting of: Southern blot analysis, Northern blot analysis and a hybridization method on a DNA-microarray.

7. The method according to claim 4 wherein said amplification method is selected from the group consisting of: a TaqMan analysis, a differential RNA display analysis and a representational difference analysis.

* * * * *